United States Patent [19]

Baumann et al.

[11] 4,272,456
[45] Jun. 9, 1981

[54] DERIVATIVES OF 8-DEHYDRO-VITAMIN A AND THEIR PREPARATION

[75] Inventors: Manfred Baumann, Mannheim; Werner Hoffmann, Neuhofen, both of Fed. Rep. of Germany

[73] Assignee: BASF Aktiengesellschaft, Fed. Rep. of Germany

[21] Appl. No.: 3,021

[22] Filed: Jan. 12, 1979

Related U.S. Application Data

[62] Division of Ser. No. 895,640, Apr. 12, 1978.

[30] Foreign Application Priority Data

Apr. 21, 1977 [DE] Fed. Rep. of Germany ....... 2717737

[51] Int. Cl.$^3$ .......................... C07C 21/02; C07F 9/54
[52] U.S. Cl. ........................................ 570/186; 568/9; 568/824
[58] Field of Search .......................... 260/656 R, 654 R

[56] References Cited

U.S. PATENT DOCUMENTS

| | | | |
|---|---|---|---|
| 2,809,216 | 10/1957 | Inhoffen | 260/654 R X |
| 2,842,599 | 7/1958 | Isler et al. | 260/654 R X |
| 2,912,474 | 11/1959 | Oroshnik | 260/654 R |
| 4,014,946 | 3/1977 | Labovitz et al. | 260/654 R |
| 4,075,257 | 2/1978 | Close et al. | 260/654 R X |

Primary Examiner—Helen M. S. Sneed
Attorney, Agent, or Firm—Keil & Witherspoon

[57] ABSTRACT

New derivatives of 8-dehydro-vitamin A obtained by vinylating or ethynylating and subsequently partially hydrogenating, 1-[3-methyl-octa-1-yne,3,5,-dien-7-on-1-yl]-2,6-dimethyl-cyclohex-1-ene or its 5- and/or 6-methyl derivatives, converting the resulting alcohols to the corresponding derivatives of 8-dehydro-vitamin A halides by reacting with thionyl chloride or phosgene, and if required converting the resulting alcohols or halides to the corresponding trialkylphosphonium salts or triarylphosphonium salts, or reacting the 8-dehydro-vitamin A halide derivatives with alkali metal salts or alkaline earth metal salts or anhydrides of lower carboxylic acids. The new compounds can be partially hydrogenated to the corresponding polyene compounds, in which case the cis-trans isomer mixtures first obtained can be rearranged in the conventional manner to the physiologically active all-trans compounds. Accordingly, the process provides a method for the total synthesis of vitamin A, and of other compounds of the carotinoid series, which is independent of the Wittig ylide synthesis.

4 Claims, No Drawings

DERIVATIVES OF 8-DEHYDRO-VITAMIN A AND THEIR PREPARATION

This is a division of application Ser. No. 895,640, filed Apr. 12, 1978.

The present invention relates to new derivatives of 8-dehydro-vitamin A of the general formula I

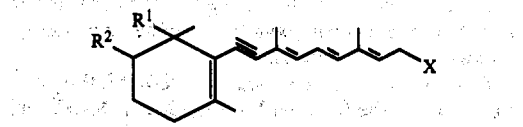

where $R^1$ and $R^2$ are hydrogen or methyl and X is chlorine, bromine, —O—CO-alkyl of 2 to 16 carbon atoms, preferably —O—CO—CH$_3$, —O—CO—C$_2$H$_5$ or —O—CO—(CH$_2$)$_{14}$—CH$_3$, or is P(R$^3$)$_3$Y, where the radicals R$^3$ are identical or different saturated or aromatic hydrocarbon radicals each of a total of up to 10 carbon atoms, preferably phenyl or toluyl, and Y is one equivalent of a strong inorganic acid, and to a process for the preparation of these compounds.

It is an object of the present invention to enrich carotenoid chemistry by providing new intermediates which on the one hand can be prepared from readily and economically accessible starting compounds and on the other hand provide a novel advantageous method for the preparation of vitamin A and related compounds, which method is independent or substantially independent of the conventional industrial Wittig ylide synthesis. The provision of such a novel method is advantageous since the use of triphenylphosphines, necessary in the Wittig reaction, suffers from disadvantages because of the toxicity of these compounds and because of pollution of the environment resulting from the formation of the large stoichiometric amounts of phosphine oxide.

We have found that these objects are achieved and that derivatives of 8-dehydro-vitamin A of the general formula I

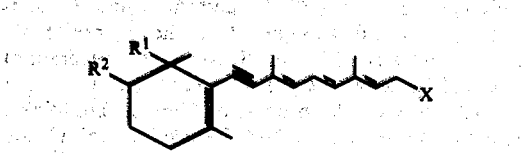

where $R^1$ and $R^2$ are hydrogen or methyl and X is chlorine, bromine, —O—CO—alkyl of 2 to 16 carbon atoms, preferably —O—CO—CH$_3$, —O—CO—C$_2$H$_5$ or —O—CO—(CH$_2$)$_{14}$—CH$_3$, or is P(R$^3$)$_3$Y, where the radicals R$^3$ are identical or different saturated or aromatic hydrocarbon radicals each of a total of up to 10 carbon atoms, preferably phenyl or toluyl, and Y is one equivalent of a strong inorganic acid, are obtained by a remarkable sequence of reactions if (a) a cyclohexene derivative of the general formula II

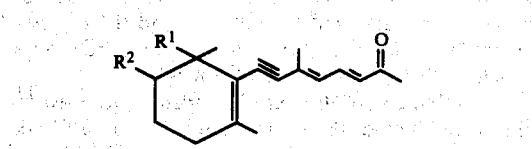

where $R^1$ and $R^2$ are hydrogen or methyl, is converted by a conventional method, either by a Grignard reaction with a solution of a vinyl-magnesium chloride or bromide or by ethynylation and subsequent partial hydrogenation, into the new alcohol of the general formula III

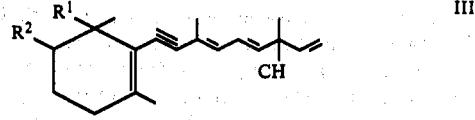

(b) if X in the desired product of the general formula I is Cl or Br, this alcohol III is converted by means of thionyl chloride or phosgene or the bromine analogs of these chlorinating agents or HBr into the desired product of the formula I, where X is Cl or Br, (c) if X in the desired product of the general formula I is P(R$^3$)$_3$Y, either (c.1) the alcohol III is converted to the desired product of the formula I by means of P(R$^3$)$_3$.HY or a mixture of P(R$^3$)$_3$ and HY at from −50° to +50° C., or (c.2) step (b) is carried out and the halogen compound obtained as described in (b) is converted to the phosphonium salt I by reaction with P(R$^3$)$_3$ at from −50° to +50° C., or (d) if X in the desired product of the general formula I is —O—CO-alkyl, step (b) is carried out and the halogen compound obtained as described in (b) is reacted, at from −30° to +50° C., preferably from −10° to +20° C., with an alkali metal salt or alkaline earth metal salt of the corresponding alkylcarboxylic acid HX, with the corresponding free alkylcarboxylic acid HX or with the anhydride of this acid.

The starting compounds II, amongst which 1-[3-methylpent-1-yn-3-en-5-al-1-yl]-2,6,6-trimethyl-cyclohex-1-ene is particularly important, are described in J. Chem. Soc. 1952, 1094 et seq. are readily obtainable, by aldol condensation of compounds IV

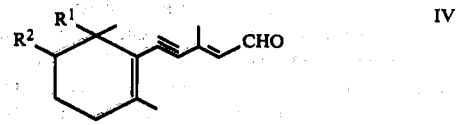

with acetone.

The compounds IV, for their part, are obtainable in an economically and industrially advantageous manner by reacting the corresponding compounds V

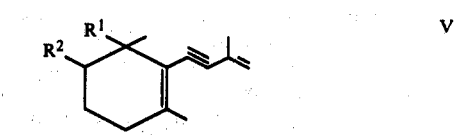

with alkyl orthoformates in the presence of acid condensing agents, eg. BF$_3$, and then dealkoxylating the compounds VI first obtained

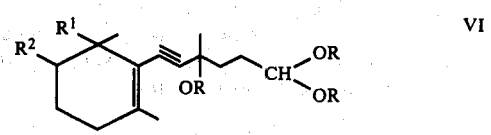

where R is lower alkyl.

Re (a)

The conversion of the cyclohexene derivative of the formula II to the new alcohol III by a Grignard reaction with a vinyl-magnesium halide is in general carried out by the conventional method for Grignard reactions, at from about −20° to +70° C., preferably from 0° to 40° C. The preparation of the vinyl-magnesium halide solution may be carried out in the conventional manner by reacting vinyl chloride or vinyl bromide with magnesium in an ether solvent, eg. diethyl ether, tetrahydrofuran or diethylene glycol dimethyl ether. The solutions used generally have a molarity of from 0.5 to 5, preferably from about 1 to 2. To achieve substantially complete conversion of the ketone it is advantageous to use about a 10% molar excess of the vinyl-Grignard compound. The alcohol III may be obtained from the reaction mixture in the conventional manner by hydrolyzing, separating off the organic phase and fractionally distilling the latter.

Ethynylation of the cyclohexene derivatives of the formula II may be carried out either by reaction with a solution of ethynyl-magnesium halide under the conditions described for the reaction with vinyl-magnesium halide, or by reaction with acetylene in an inert organic solvent in the presence of a heavy metal acetylide, eg. copper acetylide or silver acetylide, or in the presence of a basic catalyst, eg. sodium acetylide, potassium acetylide or an oxide, hydroxide, alcoholate or amide of an alkali metal or alkaline earth metal, or in the presence of an anion exchanger containing quaternary ammonium groups (cf., for example, Belgian Pat. No. 725,275).

It is particularly advantageous to carry out the reaction with acetylene in the presence of sodium, potassium, lithium or magnesium acetylide or of a compound which can form such an acetylide under the reaction conditions, eg. an oxide, hydroxide, alcoholate or amide of these metals, and in a solvent, eg. ammonia, diethyl ether, tetrahydrofuran, N-methylpyrrolidone or dimethylformamide. The ethynylation is generally carried out at from −20° to +50° C., preferably from −5° to +30° C., at pressures from atmospheric pressure to about 30 atmospheres. The reaction product may be worked up and isolated by hydrolysis and fractional distillation of the organic phase, as described above.

The partial hydrogenation of the resulting acetylene alcohol to give the alcohol of the formula III may be carried out in the absence or pressure of a solvent; the latter is particularly advantageous. Particularly suitable solvents are alcohols, eg. methanol or ethanol, ethers, eg. tetrahydrofuran, diethyl ether, dioxane and trioxane, and esters, eg. ethyl acetate and methyl propionate.

Particularly suitable catalysts are those comprising from 0.01 to 5 percent by weight of palladium on a carrier; specific examples of carriers are calcium carbonate, aluminum oxide and silicon dioxide. To increase the selectivity, it is advantageous to deactivate the said catalysts, for example in accordance with German Pat. No. 1,115,238 by treatment with zinc ions or lead ions.

The partial hydrogenation is in general carried out under atmospheric pressure or under an excess hydrogen pressure of from 0.1 to 1 atmosphere and at from about 0° to 80° C., preferably from 15° to 35° C.

Under the stated conditions, the triple bond adjacent to the cyclohexene ring is attacked substantially more slowly than the terminal triple bond.

Re (b)

The preparation of the halogen derivative I from the alcohol III may also be carried out in the conventional manner.

The amount of the halogenating agent (which is advantageously added to the solution of III first introduced into the reactor) is preferably equimolar to III, but a slight molar excess may prove advantageous in assisting completion of the reaction.

This reaction in general takes place particularly efficiently, in the desired direction, at from −30° to +20° C. or, if using HBr, at from −80° to −60° C. Examples of suitable solvents are aliphatic or aromatic hydrocarbons or chlorohydrocarbons, eg. petroleum ether, naphtha, benzene, toluene, xylene, cyclohexane, methylene chloride and chloroform.

For further syntheses in the carotinoid field, the phosphonium salts of the formula I, where X is $P(R^3)_3Y$, are of particular importance. They may be prepared by process steps (c.1) and (c.2).

Re (c.1) and (c.2)

In both cases, triphenylphosphine, which is commercially available and readily obtainable, is generally used as a starting material. Only in exceptional cases is it sometimes advisable to use other tertiary phosphines, which, whilst being mostly of equivalent value from a chemical point of view, are however also mostly more expensive, for example tritolylphosphine, tricyclohexylphosphine or tributylphosphine.

Re (c.1)

The reaction of the alcohol III with $P(R^3)_3.HY$ may be carried out either with about equimolar amounts of the acid addition salt of the phosphine $P(R^3)_3$ or with the phosphine itself, with addition of the strong acid. Suitable solvents are hydrocarbons, eg. benzene, toluene, xylene and cyclohexane, ethers, eg. diethyl ether, tetrahydrofuran and dioxane, amides, eg. dimethylformamide and N-methylpyrrolidone, alcohols, eg. methanol, ethanol, isopropanol and butanol, esters, eg. ethyl acetate, acetonitrile, benzonitrile, nitromethane, nitrobenzene, chloroform and, very particularly, polar solvents, eg. alcohols, amides and nitriles.

Particularly suitable strong acids are hydrohalic acids, eg. HCl and HBr, and sulfuric acid.

The reaction temperature is from −50° to +50° C., preferably from 0° to +30° C., and the reaction time is in general from a few minutes to 24 hours, preferably from 30 minutes to 12 hours. However, the reaction of the alcohol III with $P(R^3)_3.HY$ can also be carried out in accordance with the process of German Laid-Open Application DOS 2,537,072 in the presence of a basic compound, eg. pyridine, aniline or quinoline. In that case, the reaction temperature is preferably from 20° to 30° C., whilst in other respects the above reaction conditions apply.

Re (c.2)

The reaction of the halogen compound I with $P(R^3)_3$ is in general carried out by stirring an equimolar amount of the phosphine and the halide in a suitable solvent at the reaction temperature. If the salt precipitates, it is filtered off; soluble phosphonium salts are obtained by concentrating the solvent. Suitable solvents are those named for reaction step (c.1).

The reaction temperature is from −50° to +50° C., preferably from about 0° to +30° C., and the reaction time is in general from a few minutes to several hours, especially from 30 minutes to 24 hours.

In general, the phosphonium salts formed are used for further reactions, so that in most cases they do not need to be isolated. However, if they are required in a pure form, it is advantageous to allow them to crystallize out from dilute solution.

Re (d)

To prepare the 8-dehydro-vitamin A ester, the halogen compound I obtained as described in (b) is reacted with an alkali metal salt or alkaline earth metal salt of the corresponding alkylcarboxylic acid at from −30° to +50° C., preferably from −10° to +25° C. Suitable salts are, above all, the sodium or potassium salts. Other salts are also suitable but normally do not offer any advantages. The esterification can also be carried out with the free acid or its anhydride; however, from the point of view of working up, the use of the salts is most advantageous.

Suitable esters of the vitamin A compounds are those with alkylcarboxylic acids of 2 to 16 carbon atoms. The acetate, propionate and palmitate are of particular importance. The addition of compounds containing iodide ions, and of nitrogen compounds, eg. triethylamine and dimethylformamide, accelerates the esterification.

Conventional hydrolysis of the esters with aqueous alkali gives derivatives of the vitamin A series. It is true that 8-dehydro-vitamin A is known per se, but it may be obtained in a particularly advantageous manner by the process of the invention.

All the products I can be partially hydrogenated to the corresponding polyene compounds, in which case the cis-trans isomer mixtures first obtained can be rearranged in the conventional manner to the physiologically active all-trans isomers. The process of the invention thus provides a method for the total synthesis of vitamin A and other compounds of the carotinoid series which is independent of the Wittig ylide synthesis.

EXAMPLE 1

1-[3,7-Dimethyl-nona-1-yne-3,5,8-trien-7-ol-1-yl]-2,6,6-trimethyl-cyclohex-1-ene (III)

A solution of 15.5 g (64 mmoles) of 1-[3-methyl-octa-1-yne-3,5-dien-7-on-1-yl]-2,6,6-trimethyl-cyclohex-1-ene in a little tetrahydrofuran was added gradually, at 0° C., to 45 ml of a solution of 73 mmoles of vinyl-magnesium chloride in tetrahydrofuran. After completion of the addition, which required about 30 minutes, the reaction mixture was stirred for 12 hours at room temperature. Conventional working up gave the above product as a pale yellowish oil, in 91% yield. The structure of this alcohol was confirmed by infra-red spectroscopy and nuclear resonance spectroscopy.

IR (film): 3100–3600 (—CH); 2160 (C≡C); 1550–1640 (C=C);

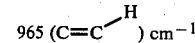

$^1$H—NMR (CDCl$_3$; TMS): δ=1.05 (s) 6 protons; 1.3 (s) 3 protons; 1.42 (m) 4 protons; 1.6–2.1 (m) 8 protons; 4.8–6.9 (m) 6 protons.

The starting compound was prepared by heating 11 g of 1-[3-methyl-penta-1-yn-3-en-5-al-1-yl]-2,6,6-trimethyl-cyclohex-1-ene with 0.2 g of KOH in solution in 3 ml of water and 80 ml of acetone. Yield, 79%.

EXAMPLE 2

1-[3,7-Dimethyl-9-chloro-nona-1-yne-3,5,7-trien-1-yl]-2,6,6-trimethyl-cyclohex-1-ene.

2.84 g (10 mmoles) of the product from Example 1 were dissolved in 10 ml of toluene and 1.3 g (11 mmoles) of thionyl chloride were added slowly at 0° C. The mixture was then stirred for 3 hours at room temperature, washed with water and dried. The above compound was obtained in virtually quantitative yield, based on the alcohol employed.

The structure was proven by IR, UV and NMR spectra.

UV: R$_{max}$=328 mμ (cyclohexane)
IR (film): 2160 (C≡C); 1550–1640 (C=C);

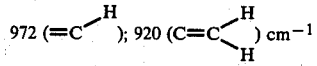

1H-NMR (CDCl$_3$, TMS) δ=1.17 (s) 6 protons; 1.55 (m) 4 protons; 1.7–2.2 (m) 11 protons; 4.25 (m) 2 protons; 5.4–7.1 (m) 4protons.

EXAMPLE 3

1-[3,7-Dimethyl-9-acetoxy-nona-1-yne-3,5,7-trien-1-yl]-2,6,6-trimethyl-cyclohex-1-ene.

3.2 g (11 mmoles) of the chlorine compound obtained as described in Example 2 were stirred for 20 hours, at room temperature, in a solution of 10 ml of toluene and 2 ml of dimethylformamide, in the presence of 0.1 g of NaI, 0.1 g of triethylamine and 1.7 g (21 mmoles) of sodium acetate. Conventional working up gave the crude 8-dehydro-vitamin A acetate in the form of a pale yellow crystal slurry. The compound was obtained pure by column chromatography (silica gel/petroleum ether/ether). The yield of pure product was 77%.

IR (film): 2170 (C≡C); 1730 (C=O); 1550–1640 (C=C); 1230 (C-O); 1020 and

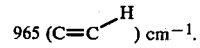

1H-NMR (CDCl$_3$, TMS): δ=1.1 (s) 6 protons; 1.48 (m) 4 protons; 1.75–2.1 (m) 11 protons; 2.0 (s) 3 protons; 4.6 (m) 2 protons; 5.4 (m) 1 proton; 5.7–6.7 (m) 3 protons.

EXAMPLE 4

1-[3,7-Dimethyl-9-bromo-nona-1-yne-3,5,7-trien-1-yl]-2,6,6-trimethyl-cyclohex-1-ene 2.84 g of the alcohol III prepared as described in Example 1 were dissolved in 50 ml of ether and an equimolar amount of a solution of HBr in ether was added dropwise at −70° C., whilst stirring. The reaction mixture was then kept for 15 minutes at from −60° to −70° C. and thereafter for 15 minutes at −15° C. 30 ml of water were then added and the organic phase was separated off, washed neutral, dried and concentrated. 3.2 g of a residue (crude yield 93.5%) were left; the structure of the material was determined by IR, NMR and UV spectroscopy.

UV: R$_{max}$=338.2 mμ in cyclohexane
IR (film): 2150 cm$^{-1}$ (C≡C); 1550–1640 cm$^{-1}$ (C=C); 1200;

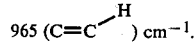

1H-NMR (CDCl$_3$; TMS): δ=1.17 (s) 6 protons; 1.55 (m) 4 protons; 1.8–2.2 (m) 11 protons; 4.15 (m) 2 protons; 5.4–7.3 (m) 4 protons.

EXAMPLE 5

1-[3,7-Dimethyl-9-palmitoyl-nona-1-yne-3,5,7-trien-1-yl]-2,6,6-trimethyl-cyclohex-1-ene This compound was prepared by a method similar to that described in Example 3, from 3.2 g of the chlorine compound obtained as described in Example 2, and 5.2 g of Na palmitate. The resulting palmitate was chromatographed and then identified by NMR, IR and UV spectra.

UV: $R_{max}$=328 mμ in cyclohexane

IR (film): 2160 (C≡C); 1730 (C=O); 1550-1640 (C=C);

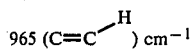

1H-NMR (CDCl$_3$; TMS) δ=0.9-1.15 (m) 30-35 protons; 1.4 (m); 1.6-1.8 (m); 2.0-2.1 (m); 4.15 (m) 2 protons; 4.9 (m) 1 proton; 5.5 (m) 2 protons; 6.0 (m) 1 proton.

EXAMPLE 6

9-[2,6,6-Trimethyl-cyclohex-1-en-1-yl]-3,7-dimethyl-nona-2,4,6-trien-8-yne-1-triphenylphosphonium bromide 1.5 g (4.3 mmoles) of the bromide obtained as described in Example 4 were dissolved in 15 ml of toluene, 1.15 g (4.4 mmoles) of triphenylphosphine were added and the reaction mixture was stirred for 12 hours at room temperature. The salt which precipitated was filtered off, washed with toluene and dried. 1.5 g of the desired phosphonium salt, having a decomposition point of 145° C., were obtained. The IR, NMR and UV spectra confirm the structure.

UV: $R_{max}$=342 mμ in cyclohexane.

We claim:

1. A derivative of 8-dehydro-vitamin A, of the general formula I

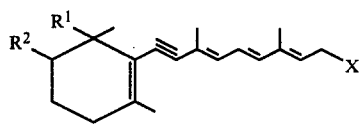

where R$^1$ and R$^2$ are hydrogen or methyl and X is chlorine or bromine.

2. A derivative of 8-dehydro-vitamin A of the general formula I

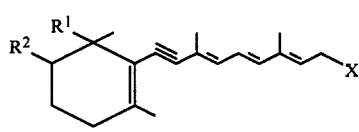

where R$^1$ is methyl, R$^2$ is hydrogen and X is chlorine or bromine.

3. A process for the preparation of a derivative of 8-dehydro-vitamin A of the general formula I

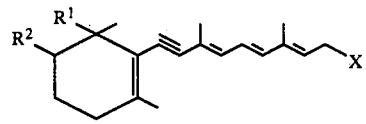

where R$^1$ and R$^2$ are hydrogen or methyl and X is chlorine or bromine, wherein (a) a cyclohexene derivative of the general formula II

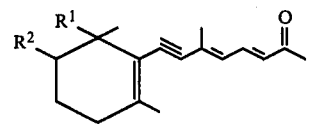

where R$^1$ and R$^2$ are hydrogen or methyl, is converted by a Grignard reaction with a solution of a vinyl-magnesium chloride or bromide into an alcohol of the general formula III

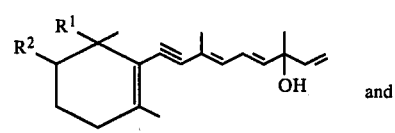

this alcohol III is converted by means of thionyl chloride chloride or phosgene or the bromine analogs of these chlorinating agents or HBr into the desired product of the formula I.

4. A process for the preparation of 8-dehydro-vitamin A of the general formula I

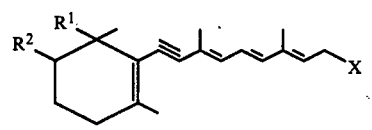

where R$^1$ and R$^2$ are hydrogen or methyl and X is chlorine or bromine, wherein
a cyclohexene derivative of the general formula II

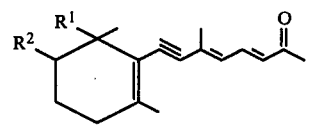

where R$^1$ and R$^2$ are hydrogen or methyl, is converted by ethynylation and subsequent partial hydrogenation into an alcohol of the general formula III

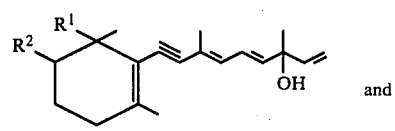

and this alcohol III is converted by means of thionyl chloride or phosgene or the bromine analogs of these chlorinating agents or HBr into the desired product of the formula I.

* * * * *